(12) United States Patent
Binns et al.

(10) Patent No.: US 11,318,203 B2
(45) Date of Patent: May 3, 2022

(54) PRODUCTION OF NANOSCALE POWDERS OF EMBEDDED NANOPARTICLES

(71) Applicant: UBICOAT LTD, Stroud (GB)

(72) Inventors: Robert Davidson Binns, Stroud (GB); Patrick William John Kinmont, Cirencester (GB)

(73) Assignee: Ubicoat Ltd, Gloucestershire (GB)

( * ) Notice: Subject to any disclaimer, the term of this patent is extended or adjusted under 35 U.S.C. 154(b) by 151 days.

(21) Appl. No.: 16/318,906

(22) PCT Filed: Jul. 18, 2017

(86) PCT No.: PCT/GB2017/052105
§ 371 (c)(1),
(2) Date: Jan. 18, 2019

(87) PCT Pub. No.: WO2018/015733
PCT Pub. Date: Jan. 25, 2018

(65) Prior Publication Data
US 2020/0171154 A1    Jun. 4, 2020

(30) Foreign Application Priority Data

Jul. 20, 2016  (GB) .................................... 1612562
Nov. 8, 2016  (GB) .................................... 1618863

(51) Int. Cl.
| | | |
|---|---|---|
| *A61K 41/00* | (2020.01) | |
| *A61K 9/16* | (2006.01) | |
| *A61K 9/51* | (2006.01) | |
| *B82Y 5/00* | (2011.01) | |

(52) U.S. Cl.
CPC ........ *A61K 41/0052* (2013.01); *A61K 9/1611* (2013.01); *A61K 9/5115* (2013.01); *A61K 9/5192* (2013.01); *B82Y 5/00* (2013.01)

(58) Field of Classification Search
CPC  A61K 41/0052; A61K 9/1611; A61K 9/5115; A61K 9/5192; B82Y 5/00
See application file for complete search history.

(56) References Cited

U.S. PATENT DOCUMENTS

| | | | |
|---|---|---|---|
| 9,597,290 B2 * | 3/2017 | Wang | ......................... B22F 9/12 |
| 2012/0003321 A1 | 1/2012 | Peng et al. | |
| 2012/0009285 A1 | 1/2012 | Yang et al. | |
| 2012/0294806 A1 | 11/2012 | Chen et al. | |
| 2015/0352210 A1 * | 12/2015 | Wang | ......................... B01J 2/02 |
| | | | 424/400 |

FOREIGN PATENT DOCUMENTS

| | | |
|---|---|---|
| CN | 104083785 A | 10/2014 |
| EP | 000066 A1 | 2/1979 |
| WO | 2004032155 A1 | 4/2004 |
| WO | 2004064921 A1 | 8/2004 |
| WO | 2006125452 A1 | 11/2006 |
| WO | 2009002569 A2 | 12/2008 |
| WO | 2015070036 A1 | 5/2015 |
| WO | 2015176025 A1 | 11/2015 |

OTHER PUBLICATIONS

Sinasi Bayrak; International Search Report and Written Opinion: International Application No. PCT/GB2017/052105; dated Oct. 23, 2017; European Patent Office; Rijswijk, Netherlands.
Dr. Natalie Cole; Combined Search and Exam Report; Great Britain Patent Application No. 1618863.3, dated Sep. 14, 2017; Great Britain Patent Office; South Wales, Great Britain.
Dr. Natalie Cole; Combined Search and Exam Report; Great Britain Patent Application No. 1612562.7; dated Sep. 12, 2016; Great Britain Patent Office; South Wales, Great Britain.
Bogden Oprea et al.; "Dispersion and Functionalization of Nanopartides Synthesized by Gas Aggregation Source: Opening New Routes Towards the Fabrication of Nanoparticles for Bio-Medicine"; Langmuir vol. 31; pp. 13813-13820; Dec. 6, 2015; ACS Publications; Washington, D.C.

(Continued)

*Primary Examiner* — Robert A Wax
*Assistant Examiner* — Olga V. Tcherkasskaya
(74) *Attorney, Agent, or Firm* — Stevens & Showalter LLP

(57) ABSTRACT

The invention provides a liquid-dispersible powder comprising nanoscale grains of matrix embedded with one or more isolated nanoparticles and a composition for the magnetic nanoparticle hyperthermia (MNH) treatment of tumours comprising nanoscale grains of matrix material containing one or more isolated nanoparticles. The invention also provides a method of production of a liquid-dispersible powder described herein, the method comprising the steps of providing nanoparticles prepared under ultra-high vacuum (UHV) gas phase conditions; co-depositing the nanoparticles within a matrix material under UHV gas phase conditions; and grinding the film to a fine powder comprising grains of groups of matrix material isolated nanoparticles. The invention also provides a method of reducing the agglomeration of nanoparticles in liquid, the method comprising isolating nanoparticles in nanoscale grains of matrix material, and the use of a liquid-dispersible powder comprising nanoscale grains of matrix material containing one or more isolated nanoparticles in the manufacture of a medicament for the MNH treatment of tumours.

7 Claims, 1 Drawing Sheet

(56) References Cited

OTHER PUBLICATIONS

L. G. Silva et al.; "Synthesis of Fe Nanoparticles Functionalized with Oleic Acid Synthesized by Inert Gas Condensation"; Journal of Nanomaterials vol. 2014; pp. 1-6, Sep. 18, 2014; Hindawi Publishing Corporation; Cairo, Egypt.

M.E. Sadat et al.; "Effect of Spatial Confinement on Magnetic Hyperthermia via Dipolar Interactions in $Fe_3O_4$ Nanoparticles for Biomedical Applications"; Materials Science & Engineering C vol. 42; pp. 52-63; Apr. 2014; Elsevier Publishing; New York City, New York.

Jianbo Li et al.; "Magnetocaloric Effect in Magnetothermally-responsive Nanocarriers for Hyperthermia-Triggered Drug Release"; Nanotechnology 23; pp. 1-10; Nov. 26, 2012; IOP Publishing; Bristol, UK.

F.M. Martin-Saavedra et al.; "Magnetic Mesoporous Silica Spheres for Hyperthermia Therapy"; Acta Biomaterialia 6; pp. 4522-4531; Jun. 30, 2010; Elsevier Publishing; New York City, New York.

Gianni Ciofani et al.; "A Bi-Modal Approach Against Cancer: Magnetic Alginate Nanoparticles for Combined Chemotherapy and Hyperthermia"; Medical Hypothesis 73; pp. 80-82; Jan. 31, 2009; Elsevier Publishing; New York City, New York.

Chris Binns et al.; "Preparation of Hydrosol Suspensions of Elemental and Core-Shell Nanoparticles by Co-Deposition with Water Vapour from the Gas-Phase in Ultra-High Vacuum Conditions"; Journal of Nanoparticle Research vol. 14; pp. 1-16; Aug. 28, 2012; Springer Publishing; New York City, New York.

Anna Corrias et al.; "Evolution of the Structure and Magnetic Properties of FeCo Nanoparticles in an Alumina Aerogel Matrix"; Chemistry of Materials 16; pp. 3130-3138; Jul. 9, 2004; ACS Publications; Washington. D.C.

Otavio Santini et al.; "Structural and Magnetic Properties of Fe and Co Nanoparticles Embedded In Powdered $Al_2O_3$": Journal of Colloid and Interface Science 289; pp. 63-70; Apr. 27, 2005; Elsevier Publishing; New York City, New York.

Ali Shokuhfar et al.; "The Heating Effect of Iron-Cobalt Magnetic Nanofluids in an Alternating Magnetic Field Application in Magnetic Hyperthermia Treatment"; Nanoscale Research Letters 8; pp. 1-11; Dec. 20, 2013 Springer Publishing; New York City, New York.

Cuilian Tao et al.: "Magnetic Mesoporous Silica Nanoparticles for Potential Delivery of Chemotherapeutic Drugs and Hyperthermia"; Dalton Transactions vol. 43; pp. 15482-15490; Aug. 21, 2014; The Royal Society of Chemistry 2014; United Kingdom.

S.R.KIM et al.; "Magnetic Properties of As-Deposited Fe—Al—O Alloy Films"; Journal of Applied Physics 87 No. 9; May 1, 2000; pp. 6262-6264; AIP Publishing; Melville, New York.

J.C. Sohn et al.; "Nanogranular Co—Fe—Al—0 Sputtered Thin Films for Magnetoelastic Device Applications in the GHz Frequency Range"; Journal of Magnetism and Magnetic Materials 272-276; 2004; pp. 1500-1502; Elsevier Publishing; New York City, New York.

\* cited by examiner ered from the prior art.

PRODUCTION OF NANOSCALE POWDERS OF EMBEDDED NANOPARTICLES

The present invention relates to the use of water-dispersible powder comprising nanoscale grains of a matrix material containing one or more isolated nanoparticles, in particular, magnetic nanoparticles. The powder of the present invention may be further dispersed in liquid, such as water, for use in medical treatments including magnetic nanoparticle hyperthermia (MNH) of tumours.

BACKGROUND TO THE INVENTION

It is well known that nanoparticles with sizes less than about 10 nm display special magnetic, optical and chemical properties that provide them with a very high performance in various applications. The most flexible way to synthesise nanoparticles is to use ultra-high vacuum (UHV) gas-phase methods that enable very good size control, flexibility of the constituent elements and the ability to produce complex core-shell and alloy structures. Although the method is costly compared to chemical synthesis, it enables the production of nanoparticles with unparalleled performance in certain high-end applications.

One of these high-end applications is the MNH treatment of tumours. This is a radical nanotechnology-based therapy that uses magnetic nanoparticles to raise the temperature of a tumour by a few degrees thus encouraging apoptosis of the cancer cells without harming surrounding tissue. As all cancers respond in the same way to heat this is a generically useful therapy. However, it has been found that the currently available iron oxide (FeO) nanoparticles used do not produce sufficient heat for a general tumour therapy.

One way to combat this is to use UHV gas-phase produced nanoparticles containing a pure iron (Fe) core and a biocompatible shell, for example FeO (Fe@FeO particles). Such particles have been shown to produce an order of magnitude more heat per gram of material. Such particles necessarily have to be produced in UHV conditions to avoid oxidising the Fe core.

However, despite addressing the heat requirement issue using advances in nanoparticle technology, a generic problem with all nanoparticles is their tendency to agglomerate, which always degrades their performance. This is also true in the case of core/shell nanoparticles.

Although a method has been developed to deposit these in water for medical applications, they rapidly agglomerate, which reduces their heating performance.

There is therefore a need for a method to reduce the agglomeration of nanoparticles, and in particular magnetic nanoparticles, in fluid such as water so that the advantageous properties of nanoparticles can be exploited whilst minimising the heating and other property compromises due to agglomeration.

It is an object of the present invention to address the problems of the prior art.

STATEMENTS OF INVENTION

A first aspect of the present invention provides a liquid-dispersible powder comprising nanoscale grains of a matrix material composed of one or more biocompatible oxides, in which the matrix material contains a plurality of isolated nanoparticles, wherein each nanoparticle comprises a magnetic core selected from one or more of Fe or an alloy of Fe/Cobalt (Co).

The liquid-dispersible powder may for example be a water-dispersible powder.

The term "nanoparticles" used herein is intended to include simple elemental, core/shell, and alloy structures.

The biocompatible oxide is any suitable oxide capable of being sputter coated to form a matrix or shell, preferably a matrix. Sputter coating is a deposition process to cover a substrate with a thin layer of material. Any suitable method of sputter coating may be used. For example, the oxide coatings may for example be provided or deposited, for example co-deposited, using a pulsed or radio frequency (RF) power supply at approximately 100 W and a gas pressure of approximately 0.1 mbar.

Suitable oxides include, but are not limited to aluminium oxide/alumina ($Al_2O_3$). The biocompatible oxide shell is preferably thermally stable. Preferably, the biocompatible oxide is stable at ambient pressure and at temperatures around the temperature of the human body. In one embodiment, the biocompatible oxide is stable at ambient pressure and at a temperature of at least 37° C., preferably at least 40° C., more preferably at least 45° C., for example at least 50° C. The term stable is used herein to refer to the biocompatible oxide remaining intact within the powder without any degradation, such as for example thermal degradation, under the conditions described herein.

A second aspect of the present invention provides a composition for the MNH treatment of tumours comprising nanoscale grains of a matrix material composed of one or more biocompatible oxides, in which the matrix material contains a plurality of isolated nanoparticles, wherein each nanoparticle comprises a magnetic core selected from one of more of Fe or an alloy of Fe/Co.

A third aspect of the present invention provides a method of production of a liquid-dispersible powder according to any preceding claim, the method comprising the steps of:
  a. providing nanoparticles prepared under UHV gas phase conditions, wherein each nanoparticle comprises a magnetic core selected from one of more of Fe or an alloy of Fe/Co;
  b. co-depositing the nanoparticles within a matrix composed of one or more biocompatible oxides under UHV gas phase conditions;
  c. grinding the film to a fine powder comprising grains of groups of matrix isolated nanoparticles.

The grinding step may comprise ball milling, however, any suitable method may be used to grind the film provided it results in a suitably fine powder. The resultant powder has to be sufficiently fine to pass through the smallest capillary of the body.

A fourth aspect of the present invention provides a method of reducing the agglomeration of nanoparticles in water, the method comprising isolating a plurality of nanoparticles in nanoscale grains of a matrix material composed of one or more biocompatible oxides, wherein each magnetic nanoparticle comprises a magnetic core selected from one of more of Fe or an alloy of Fe/Co.

A fifth aspect of the present invention provides a liquid-dispersible powder comprising nanoscale grains of a matrix material composed of one or more biocompatible oxides, in which the matrix material contains a plurality of isolated nanoparticles, wherein each magnetic nanoparticle comprises a magnetic core selected from one of more of Fe or an alloy of Fe/Co in the MNH treatment of tumours.

MNH is an emerging cancer treatment, based on the fact that magnetic nanoparticles produce heat when exposed to an alternating magnetic field. By targeting the magnetic nanoparticles to the tumours either by the body's natural processes such as the enhanced permeability and retention effect (EPR), magnetic targeting or biological targeting, then exposing the cells to an alternating magnetic field of predetermined amplitude and frequency, the cell temperature would rise thereby encouraging apoptosis of the cells without harm to surrounding tissues.

However, one drawback to such a treatment is that the magnetic nanoparticles have to be dispersed in a liquid before they can be delivered to the body, for example into the bloodstream. Dispersal of magnetic nanoparticles in liquid leads to agglomeration with consequential altering of the desirable properties of the particles. By embedding the nanoparticles within a matrix material of the powder of the present invention, the nanoparticles are inherently spatially separated from one another and agglomeration is minimised. The nanoscale nature of the grains of matrix material are sufficiently big to contain a plurality of nanoparticles per grain whilst remaining small enough to be liquid-dispersible, for example water-dispersible, and therefore useful in medical applications.

In any aspect of the present invention, the nanoscale grains are preferably provided in the form of a liquid-dispersible powder, for example a water-dispersible powder. Alternatively, the composition may be provided in the form of a liquid-based solution, for example water-based solution, in which the grains of matrix have already been dispersed.

Typically, the nanoparticles are around 15 nm in diameter. As a nanoscale grain of matrix material may be as large as 100 nm in width, it can therefore be appreciated that each grain of matrix material may retain several embedded nanoparticles therein thereby allowing the dispersal of nanoparticles, and particularly magnetic nanoparticles, within liquid such as but not limited to water, whilst minimising agglomeration.

As mentioned above, at least a portion of the nanoparticles comprise magnetic nanoparticles. In one embodiment, each magnetic nanoparticle may comprise a magnetic core, such as for example an Fe core and/or an alloy core comprising Fe/Co, encased in a biocompatible shell, composed of for example one more of: FeO, gold (Au), or silver (Ag), or any combination thereof. For example, the magnetic nanoparticles may be composed of FeO (Fe@FeO), Au (Fe@Au) or Ag (Fe@Ag) particles, or any combination thereof. However, it is to be appreciated that the present invention may be carried out using magnetic nanoparticles of alternative composition.

Preferably, the nanoparticles are isolated in the matrix under UHV gas phase conditions.

The matrix material protects the magnetic nanoparticles by preventing oxidation of the nanoparticles. The matrix material thereby helps to ensure that the magnetic properties of the nanoparticles are retained within, and during use of, the powder.

DESCRIPTION OF THE DRAWINGS

Embodiments of the present invention will now be described by way of example only and with reference to the following FIGURES.

SPECIFIC DESCRIPTION

Magnetic nanoparticles with an Fe core surrounded by a biocompatible shell, for example FeO, which are otherwise referred to as Fe@FeO nanoparticles, were produced using UHV gas-phase methods. It is however to be understood that the present invention is not limited to magnetic nanoparticles comprising an Fe core. The nanoparticles may comprise other magnetic cores, such as for example alloy cores such as for example Fe/Co alloy cores. It is also to be understood that the biocompatible shell is not limited to being composed of FeO. The biocompatible shell may be composed of one or more of: FeO, Au or Ag particles, or any combination thereof. The nanoparticles may for example comprise one or more of an Fe core surrounded with FeO (Fe@FeO), an Fe core surrounded with Au (Fe@Au), or an Fe core surrounded with Ag (Fe@Ag), or any combination thereof. The use of UHV gas-phase methods facilitates the production of magnetic nanoparticles having a relatively narrow size distribution of around 10 nm in size, whilst minimising nanoparticle agglomeration. Uncontrolled particle agglomeration would adversely affect the desirable properties of the nanoparticles.

The nanoparticles, for example Fe@FeO nanoparticles, are then co-deposited within a matrix under UHV conditions to produce a thin film with embedded isolated magnetic nanoparticles. The matrix material may be any material capable of sputter coating. Suitable oxides include, but are not limited to $Al_2O_3$. Any suitable method of sputter coating of the nanoparticles with the matrix material may be used. For example, the oxide coatings may for example be provided using a pulsed or RF power supply at approximately 100 W and a gas pressure of approximately 0.1 mbar. It is however to be understood that the method of depositing nanoparticles within the matrix material is not to be limited to these process parameters.

Figure 1B:
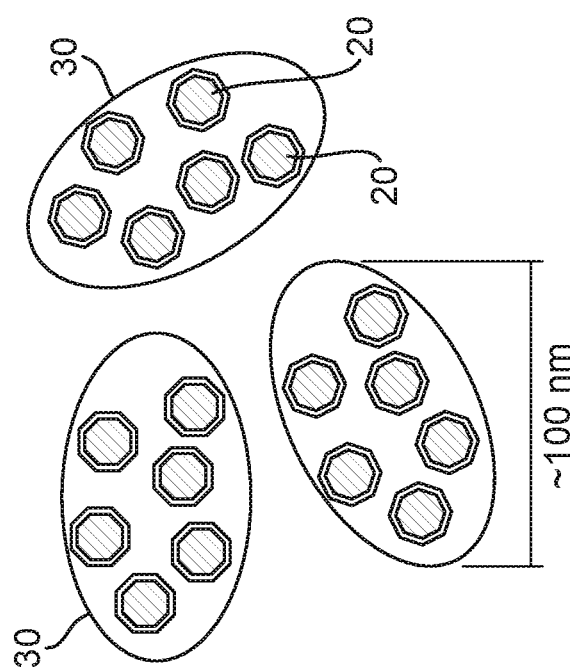
FIG. 1(b) shows nanoscale grains of matrix with embedded nanoparticles after milling, in accordance with the embodiment of FIG. 1.
Figure 1A:
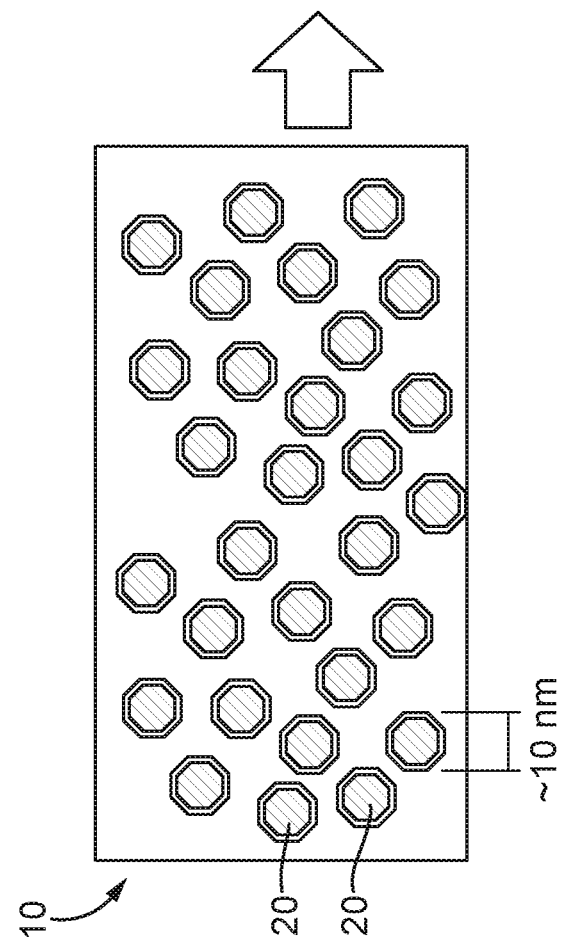
FIG. 1(a) shows a thin film of matrix with embedded nanoparticles prior to milling, in accordance with a first embodiment of the present invention.

FIG. 1(a) shows such a thin film matrix 10 with embedded nanoparticles 20 isolated within the film 10. As can be seen from FIG. 1, there is no agglomeration of the nanoparticles 20 within the film 10 and each nanoparticle 20 is spatially isolated from neighbouring nanoparticles 20.

In order to use the magnetic nanoparticles in medical applications, the nanoparticles must be liquid-dispersible, for example water-dispersible. Therefore, the thin film was subjected to grinding by a ball mill to produce a fine powder of nanoscale grains 30 of matrix containing small groups of embedded magnetic nanoparticles 20. FIG. 1(b) shows the film 10 of FIG. 1 after the milling process. Nanoscale grains 30 of matrix 10 are shown, each approximately 100 nm in size, each grain 30 having a group of embedded magnetic nanoparticles 20 clearly spatially isolated from one another.

It should be noted that the nanoscale grains 30 of matrix 10 isolated nanoparticles 20 as shown in FIG. 1(b) which are each approximately 100 nm in size are still small enough for use in medical applications such as the MNH treatment of tumours or bacterial infections. The size of each nanoscale grain 30 is still at least 100 times smaller than the finest capillaries in the human body.

In order to use the fine powder of nanoscale grains 30 in medical applications, the fine powder must be dispersed in liquid. The nanoscale dimensions of the grains 30 facilitates efficient dispersal of the grains 30 in liquid, such as but not limited to water. The fine powder may be added to water to provide a liquid composition comprising nanoscale grains of matrix embedded with a plurality of isolated nanoparticles which can be used for medical applications such as, but not restricted to MNH treatment of cancer tumours.

This embodiment of the present invention demonstrates how a suspension of magnetic nanoparticles can be produced for medical applications whilst avoiding the typical problems of agglomeration. It should be noted that due to the arrangement of embedded nanomagnetic particles within the thin matrix of each grain 30, even if some agglomeration of grains 30 within a liquid is experienced, the magnetic nanoparticles will remain spatially isolated from one another, thereby retaining their desirable properties.

Finally, it is to be appreciated that the milling process itself will result in some modification of the individual nanoparticles. For example, the strain induced by the milling process would alter the magnetic anisotropy of the nanoparticles. Therefore, the milling process itself can be used as an additional way of controlling the characteristics of the nanoparticles and the performance of the final fine powder.

Although the example refers to the use of Fe@FeO nanoparticles it is to be understood that the present invention is not limited to magnetic nanoparticles comprising an Fe core coated in a biocompatible shell comprising FeO. The magnetic nanoparticles may comprise a core selected from one or more of Fe or an alloy of Fe/Co. The biocompatible shell may comprise one or more of FeO, Au, or Ag, or any combination thereof

The invention claimed is:

1. A liquid-dispersible powder comprising nanoscale grains of a matrix material composed of one or more biocompatible oxides, wherein the nanoscale grains of the matrix material have a diameter of less than 100 nm, wherein the matrix material contains a plurality of nanoparticles spatially isolated from one another, wherein the spatially isolated nanoparticles are not agglomerated, and wherein each nanoparticle comprises a magnetic core comprising one or more of iron or an alloy of iron/cobalt.

2. A method for the magnetic nanoparticle hyperthermia treatment of tumours comprising:
   preparing a composition comprising the liquid-dispersible powder of claim 1; and
   delivering the composition to a body of a patient.

3. The liquid-dispersible powder of claim 1, wherein each nanoparticle comprises a magnetic core selected from one or more of iron or an alloy of iron/cobalt encased in a biocompatible shell.

4. The liquid-dispersible powder of claim 3, wherein the biocompatible shell comprises one or more of iron oxide, gold, or silver, or any combination thereof.

5. A method of production of the liquid-dispersible powder of claim 1, the method comprising:
   a. providing nanoparticles prepared under ultra-high vacuum (UHV) gas phase conditions, wherein each magnetic nanoparticle comprises a magnetic core selected from one or more of iron or an alloy of iron/cobalt;
   b. co-depositing, under UHV gas phase conditions, a plurality of the nanoparticles within a matrix material composed of one or more biocompatible oxides to produce a film comprising nanoparticles embedded within the matrix material and spatially isolated from one another; and
   c. grinding the film to a fine powder comprising grains, one or more of the grains comprising a plurality of nanoparticles spatially isolated from one another within the matrix material, wherein the spatially isolated nanoparticles are not agglomerated.

6. The method of claim 5, wherein grinding the film to a fine powder comprises ball milling.

7. The method of claim 5, wherein each magnetic nanoparticle comprises a magnetic core selected from one or more of iron or an alloy of iron/cobalt encased in a biocompatible shell.

\* \* \* \* \*